(12) United States Patent
Choi et al.

(10) Patent No.: US 9,916,656 B2
(45) Date of Patent: Mar. 13, 2018

(54) METHOD FOR PROCESSING RADIOGRAPHIC IMAGE AND RADIOGRAPHY SYSTEM

(71) Applicant: DRTECH CORP, Seongnam-Si, Gyeonggi-Do (KR)

(72) Inventors: Ho Yeol Choi, Gwangmyeong-Si (KR); Choul Woo Shin, Seongnam-Si (KR); Mi Jung Jo, Yongin-Si (KR); Eun Kim, Seongnam-Si (KR); Jeong Pil Kim, Seoul (KR); Yong Ju Na, Gwangju-Si (KR)

(73) Assignee: DRTECH CORP (KR)

( * ) Notice: Subject to any disclaimer, the term of this patent is extended or adjusted under 35 U.S.C. 154(b) by 93 days.

(21) Appl. No.: 14/912,085

(22) PCT Filed: Oct. 23, 2015

(86) PCT No.: PCT/KR2015/011288
§ 371 (c)(1),
(2) Date: Feb. 12, 2016

(87) PCT Pub. No.: WO2017/034075
PCT Pub. Date: Mar. 2, 2017

(65) Prior Publication Data
US 2017/0262976 A1    Sep. 14, 2017

(30) Foreign Application Priority Data
Aug. 26, 2015 (KR) .................. 10-2015-0120500

(51) Int. Cl.
*G06T 7/00* (2017.01)
*G06T 5/00* (2006.01)
*A61B 6/00* (2006.01)

(52) U.S. Cl.
CPC .......... *G06T 7/0012* (2013.01); *A61B 6/4233* (2013.01); *A61B 6/5282* (2013.01); *G06T 5/00* (2013.01); *G06T 2207/10116* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,638,752 | B2 * | 12/2009 | Partain | H04N 5/361 |
| | | | | 250/214 C |
| 9,649,086 | B2 * | 5/2017 | Tajima | A61B 6/563 |

(Continued)

FOREIGN PATENT DOCUMENTS

| | | |
|---|---|---|
| JP | 10314152 | 12/1998 |
| JP | 2000245721 | 9/2000 |

(Continued)

*Primary Examiner* — Tsung-Yin Tsai
(74) *Attorney, Agent, or Firm* — Renaissance IP Law Group LLP (57) ABSTRACT

Provided is a method for processing a radiographic image including obtaining a radiographic image using an indirect radiographic detector comprising a scintillator panel and a pixel array panel, determining a parameter value for defining a point spread function (PSF) according to the scintillator panel or the pixel array panel, and correcting the radiographic image by deconvoluting the radiographic image using the PSF to which the parameter value is applied.

10 Claims, 7 Drawing Sheets

(56) References Cited

U.S. PATENT DOCUMENTS

| | | | | |
|---|---|---|---|---|
| 2003/0007601 | A1* | 1/2003 | Jaffray | A61B 6/032 378/65 |
| 2006/0067461 | A1* | 3/2006 | Yin | G06T 11/005 378/5 |
| 2008/0055305 | A1* | 3/2008 | Blank | G06T 15/08 345/419 |
| 2009/0202125 | A1* | 8/2009 | Zhao | G06T 5/003 382/131 |
| 2009/0324029 | A1* | 12/2009 | Araikum | G06T 5/003 382/128 |
| 2010/0069741 | A1* | 3/2010 | Kuhn | A61B 5/06 600/424 |
| 2010/0284596 | A1* | 11/2010 | Miao | G06T 11/005 382/131 |
| 2012/0049080 | A1* | 3/2012 | Enomoto | A61B 6/4233 250/371 |
| 2012/0163695 | A1* | 6/2012 | Hopkins | G06T 5/003 382/132 |
| 2015/0245807 | A1* | 9/2015 | Tajima | A61B 6/563 378/98 |
| 2015/0248943 | A1* | 9/2015 | Handa | G21K 1/067 378/62 |
| 2016/0109387 | A1* | 4/2016 | Pan | G01N 23/04 378/36 |

FOREIGN PATENT DOCUMENTS

| | | |
|---|---|---|
| KR | 20120012736 | 2/2012 |
| KR | 20150050728 | 5/2015 |

* cited by examiner

Line Spread Function

FIG. 3

Line Spread Function

FIG. 4

Line Spread Function

METHOD FOR PROCESSING RADIOGRAPHIC IMAGE AND RADIOGRAPHY SYSTEM

TECHNICAL FIELD

The present invention relates to a method for processing a radiographic image and a radiography system, and in particular, to a method for processing a radiographic image and a radiography system capable of correcting a blurring due to light scattering occurring in a scintillator panel of an indirect radiation detector.

BACKGROUND ART

Medical imaging using a radiation is performed on a subject matter through a Compton effect that only a portion of energy of a radiation photon is delivered to electrons or a photoelectric effect that all energy is delivered to electrons and a radiation is completely absorbed. At this point, typically a radiation having energy of 10 keV to 200 keV is used.

Digital radiography devices for obtaining a radiographic image are divided into an indirect type equipment and a direct type equipment. In the indirect type equipment, a radiation collides with a scintillator of a scintillator panel to generate a visible light ray, and the visible light ray is transformed to an image signal through a thin film transistor in which a charge coupled device (CCD) or a photodiode is installed. In addition, the direct type equipment obtains an image in a manner that a radiation passing through a subject is directly irradiated on a thin film transistor in which a photoconductor or a photoresistor is installed, and is transformed to an image signal.

In such a radiography system, a radiation radiated from a radiation generating device is irradiated on a wide area at once in a cone type and causes image distortion due to radiation scattering. As a method for removing such a scatter radiation, a method using an anti-scatter grid or an air gap is used.

The grid method uses a difference between a primary radiation almost perpendicularly incident to a radiation detector and a scatter radiation incident in a random direction. This method is to dispose the anti-scatter grid between a subject and a radiation detector, and to physically cut off the scatter radiation, which is obliquely incident in a process where a radiation passing through the subject passes through the grid, from reaching the radiation detector. Here, the anti-scatter grid is composed of lead and aluminum.

The method using the air gap is imaging with a space between a subject and a radiation detector. The scatter radiation is not perpendicularly but obliquely incident to the detector, and when there is the air gap between the detector and the subject, only the primary radiation among photons passing through the subject reaches the radiation detector. On the other hand, the scatter radiation is scattered to the surroundings and does not reach the radiation detector.

However, in a case of adopting the indirect radiation detector using the scintillator panel, although the scatter radiation caused by the subject may be removed using these methods, scattering by the scintillator inside the radiation detector is not removed. In addition, when a radiographic image is obtained by this radiography system, a blurring may occur in the radiographic image, thereby lowering the sharpness of the radiographic image.

CITATION LIST

Patent Literature

Korean Patent Laid-open Publication No. 10-2012-0012736

DISCLOSURE OF THE INVENTION

Technical Problem

The present invention provides a method for processing a radiographic image and a radiography system capable of correcting a blurring, which occurs due to scattering occurred in a scintillator panel of an indirect radiation detector, with deconvolution using a point spread function (PSF).

Technical Solution

According to an embodiment of the present invention, a method for processing a radiographic image includes: obtaining a radiographic image using an indirect radiographic detector including a scintillator panel and a pixel array panel; determining a parameter value for defining a point spread function (PSF) according to the scintillator panel or the pixel array panel; and correcting the radiographic image by deconvoluting the radiographic image using the PSF to which the parameter value is applied.

The method may further include removing a fault element from the radiographic image before the correcting the radiographic image by deconvoluting the radiographic image.

The parameter may define a magnitude of the PSF and a shape of the PSF.

In the determining a parameter value, the parameter value may be determined to allow a correction image for which the radiographic image is deconvoluted using the PSF to satisfy an image quality reference.

The image quality may be evaluated by measuring at least any one selected from among a modulation transfer function (MTF), a detective quantum efficiency (DQE), a normalized noise power spectrum (NNPS), and a signal to noise ratio (SNR).

The image quality reference may include a condition that a DQE value of the correction image is in a range of 90% to 110% of a DQE value of the radiographic image in a same spatial frequency.

The image quality reference may include a condition that for a spatial frequency of the correction image, a value of the MTF decreases according to an increase in spatial frequency, and the MTF value is a highest in the correction image according to the parameter value.

The method may further include: classifying and storing the determined parameter value according to at least any one among a pixel size of the pixel array panel, a thickness of the scintillator panel, and a type of the scintillator, wherein in the correcting the radiographic image by deconvoluting the radiographic image, the radiographic image is corrected by selecting a parameter value from among stored parameter values according to at least any one among the pixel size of the pixel array panel, the thickness of the scintillator panel, and the type of the scintillator, which are used for obtaining the radiographic image.

In the correcting the radiographic image by deconvoluting the radiographic image, the radiographic image may be corrected by iterating the deconvolution using the PSF to which the parameter value is applied.

According to another embodiment of the present invention, a radiography system includes: a radiation irradiating unit irradiating a radiation on a subject; an indirect radiation detector including a scintillator panel converting a radiation, which passes through the subject and is incident thereto, to a visible light, and a pixel array panel storing charges generated by the visible light in each pixel, and realizing a radiographic image according to a charge amount in each pixel; and an image processing unit correcting the radiographic image by deconvoluting the radiographic image obtained by the indirect radiation detector using a point spread function (PSF).

The image processing unit may include: a data storage unit in which a parameter value, which is applied to the PSF according to at least any one among a pixel size of the pixel array panel, a thickness of the scintillator panel, and a type of the scintillator, is classified and stored according to at least any one among the pixel size of the pixel array panel, the thickness of the scintillator panel, and the type of the scintillator; a parameter selecting unit selecting the parameter value according to the at least any one among a pixel size of the pixel array panel, a thickness of the scintillator panel, and a type of the scintillator; and an image correcting unit deconvoluting the radiographic image using the PSF to which the selected parameter value is applied.

The image processing unit may further include a preprocessing unit removing a fault element from the obtained radiographic image.

The image processing unit may further include an iteration setting unit setting a number of times of deconvoluting the radiographic image.

The iteration setting unit may set an iteration number for satisfying a condition that a DQE value of a correction image, which is corrected by deconvoluting the radiographic image with the PSF, is in a range of 90% to 110% of a DQE value of the radiographic image in a same spatial frequency.

Advantageous Effects

A method for processing a radiographic image according to an embodiment of the present invention may correct a blurring of a radiographic image, which is caused by scatting of light generated in a scintillator panel of an indirect radiation detector, by deconvoluting the radiographic image using a point spread function (PSF). Accordingly, a radiographic image of which the sharpness is improved with an indirect radiation detector may be obtained. In addition, since a radiographic image of which the sharpness is improved with the indirect radiation detector having a high detective quantum efficiency (DQE) is obtained, a sharp radiographic image may be obtained even with a small radiation dose and accordingly, a radiation exposure dose of a subject may be lowered.

In addition, artificial improvement in sharpness may be prevented and only a blurring may be corrected by evaluating image quality of a radiographic image in which the blurring is corrected. In addition, a parameter value having highest sharpness and satisfying the image quality according to the thickness of the scintillator panel may be easily obtained by using parameter data.

Furthermore, amplification of a defective element may be prevented in a process for correcting the blurring of the radiographic image through preprocessing for removing the defective element before correcting the blurring of the radiographic image. In addition, since the blurring is not artificially deleted but is mitigated to disappear, data information on the radiographic image may be prevented from being lost.

MODE FOR CARRYING OUT THE INVENTION

Hereinafter, specific embodiments will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the drawings and written description, like reference numerals refer to like elements. In the drawings, the dimensions may be partially enlarged or exaggerated for clarity of illustration.

A point spread function (PSF) depicts a shape that a point is represented by blurring in an image, and the extent of blurring may vary according to a shape of the PSF. For example, the larger the blurring area at each point in an image is, the blurring of the image gets more severe. Accordingly, the extent of blurring may be adjusted by adjusting the shape of the PSF, and using this, an image including the blurring may be obtained through convolution of a sharp image with the PSF.

Accordingly, through this principle, a blurring effect may be applied to the sharp image. Besides, as in the present invention, a blurring of a radiographic image may also be corrected by deconvoluting the radiographic image with a PSF. Furthermore, when the radiographic image including the blurring is corrected by performing deconvolution with the PSF, the blurring is not artificially deleted but is mitigated to disappear and accordingly data information on the radiographic image may not be lost. Accordingly, when the radiographic image is corrected, quality of the radiographic image may not be lowered.

Figure 1:
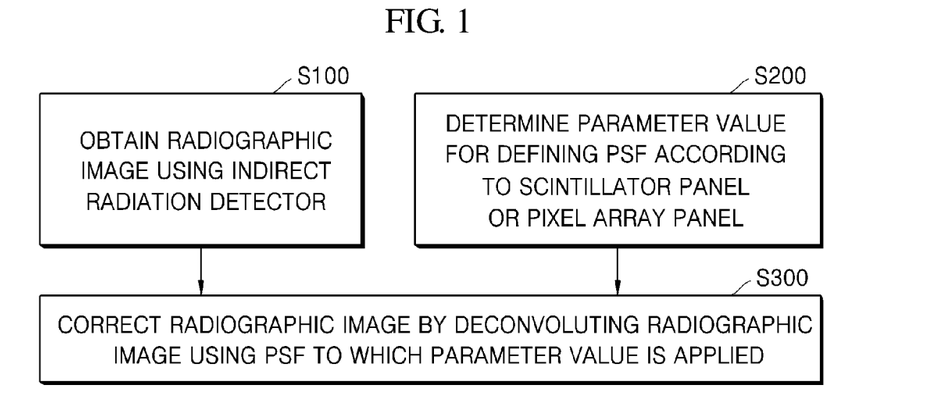
FIG. 1 is a flowchart illustrating a method for processing a radiographic image according to an embodiment of the present invention.

FIG. 1 is a flowchart illustrating a method for processing a radiographic image according to an embodiment of the present invention.

Referring to FIG. 1, a method for processing a radiographic image according to an embodiment of the present invention may include an operation S100 for obtaining a radiographic image by using an indirect radiation detector, which includes a scintillator panel 110 and a pixel array panel 120; an operation S200 for determining a value of a parameter defining a PSF according to the scintillator panel 110 or the pixel array panel 120; and an operation S300 for correcting the radiographic image by deconvoluting it with a PSF to which the parameter value is applied.

In order to process a radiographic image, the radiographic image is obtained (operation S100) using the indirect radiation detector including the scintillator 110 and the pixel array panel 120. When the radiographic image is obtained with the indirect radiation detector using the scintillator panel 110, a blurring occurs by light scattered by a scintillator 111 of the scintillator panel 110. At this point, the light scattering by the scintillator 111 may have a Gaussian shape. In order to correct the blurring and improve the sharpness of the radiographic image, the radiographic image including the blurring in the present invention is defined as an image for which a sharp image is convoluted with a PSF. In addition, the radiographic image is corrected by deconvoluting the radiographic image including the blurring using the PSF.

The pixel array panel 120 may store, for each pixel, charges generated by the visible light into which a radiation irradiated on the scintillator panel 110 is converted. Here, the resolution of the radiographic image may vary according to a pixel size of the pixel array panel 120.

In addition, the parameter value, which defines the PSF according to the scintillator panel 110 or the pixel array panel 120, is determined (operation S5200) in parallel with operation S100 for obtaining the radiographic image. Operation S200 for determining the parameter value may be concurrently performed with operation S100 for obtaining the radiographic image. Alternatively, the parameter value may be determined before or after operation S100 for obtaining the radiographic image. Here, the parameter value for defining the PSF may be determined depending on the scintillator panel 110 or the pixel array panel 120. At this point, the parameter value for defining the PSF may be determined depending on the pixel size of the pixel array panel 120, the thickness of the scintillator panel 110, or the type of the scintillator 111.

Figure 2:
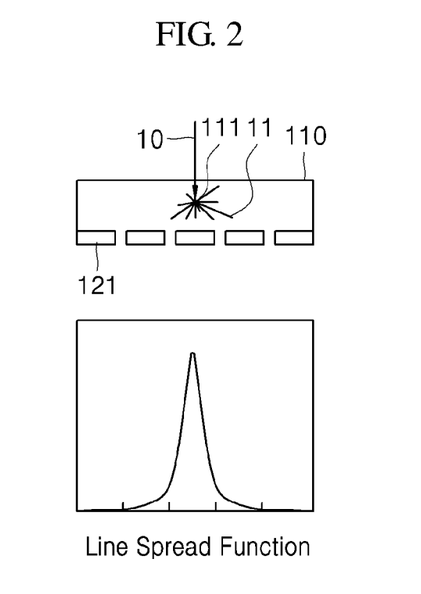
FIG. 2 is a conceptual diagram illustrating a scattering degree of light in a thin scintillator panel according to an embodiment of the present invention.
Figure 3:
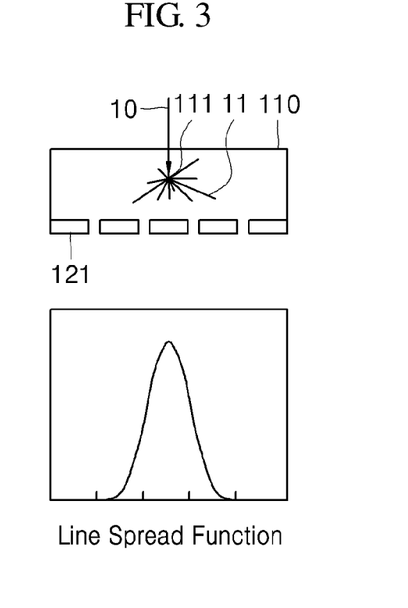
FIG. 3 is a conceptual diagram illustrating a scattering degree of light in a medium thickness scintillator panel according to an embodiment of the present invention.
Figure 4:
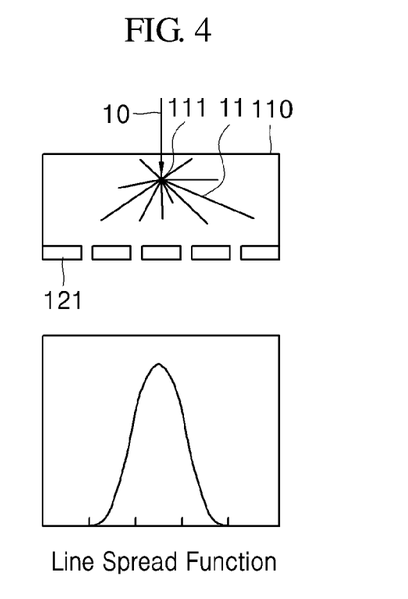
FIG. 4 is a conceptual diagram illustrating a scattering degree of light in a thick scintillator panel according to an embodiment of the present invention.

FIG. 2 is a conceptual diagram illustrating a scattering degree of light in a thin scintillator panel according to an embodiment of the present invention, FIG. 3 is a conceptual diagram illustrating a scattering degree of light in a medium thickness scintillator panel according to an embodiment of the present invention, and FIG. 4 is a conceptual diagram illustrating a scattering degree of light in a thick scintillator panel according to an embodiment of the present invention.

A line spread function (LSF) represents a distribution of a certain value one-dimensionally, and represents a distribution (or a difference in intensity) according to a position of visible light 11 emitted from any one scintillator 111 in FIGS. 2 to 4. Referring to FIGS. 2 to 4, a scattering degree of light may be checked through the PSF and the greater the scattering degree of light is, the wider the sigma (or standard deviation) of the LSF is. Accordingly, it may be seen through FIGS. 2 to 4 that the thicker the scintillator panel 110 is, the more the scattering of light is. Here, the narrower the sigma of the LSF is, the sharper the radiographic image is, and accordingly, the wider the sigma of the LSF is, the greater the scattering degree of light is. In other words, as the thickness of the scintillator panel 110 is thicker, a conversion efficiency that the radiation 10 is converted to visible light 11 becomes higher. However, when scattering of light is increased according to the conversion efficiency, it causes a more severe blurring of the radiographic image.

The scattering degree of light may vary according not only to the thickness of the scintillator panel 110 but also to the type of the scintillator panel 110 (or scintillator 111). From the FIGS. 2 to 4, the straightly incident radiation 10 collides with the scintillator 111 and is emitted from the scintillator 111 as the visible light 11 in all directions. The blurring occurs in the radiographic image by the visible light 11 incident not perpendicularly but diagonally among the visible light 11 emitted in all directions. When the conversion efficiency for converting the radiation 10 to the visible light 11 becomes better according to the type of the scintillator 111 (or the type of the scintillator panel), the light scattering is increased to cause more severe blurring.

Furthermore, the blurring of the radiographic image may vary according to the intensity of the radiation 10 incident to the scintillator panel 110. When the radiation 10 of lower energy is incident to the scintillator panel 110 and the thickness of the scintillator panel 110 is thick, the light scattering is increased. In this case, since the blurring becomes severe in the radiographic image, a spatial resolution is reduced but a speed becomes increased. On the other hand, when the radiation 10 of high energy is incident to the scintillator panel 110, since a probability that the radiation 10 reacts to the scintillator 111 becomes high as the thickness of the scintillator panel 110 becomes thicker, the spatial resolution may become better. In other words, since there is the proper thickness of the scintillator panel 110 according to the intensity of the radiation 10, when the thickness of the scintillator panel 110 is thinner than the proper one, the spatial resolution becomes bad. When the thickness of the scintillator panel 110 is thicker than the proper one, the light scattering is increased to make the blurring of the radiographic image more severe.

Figure 5:
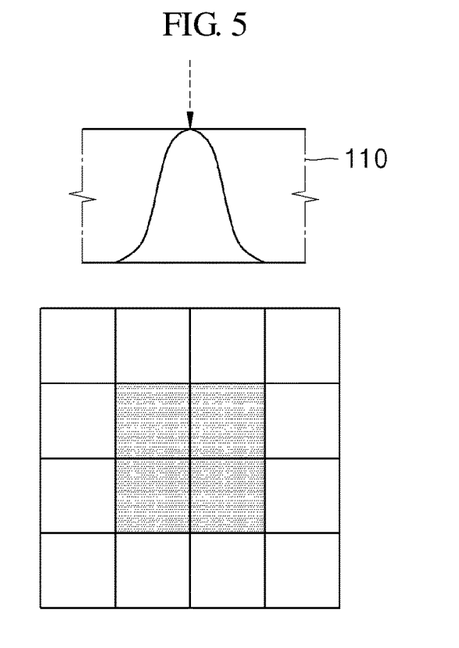
FIG. 5 is a conceptual diagram illustrating the magnitude of a point spread function (PSF) in a pixel array panel in which a pixel size is large according to an embodiment of the present invention.
Figure 6:
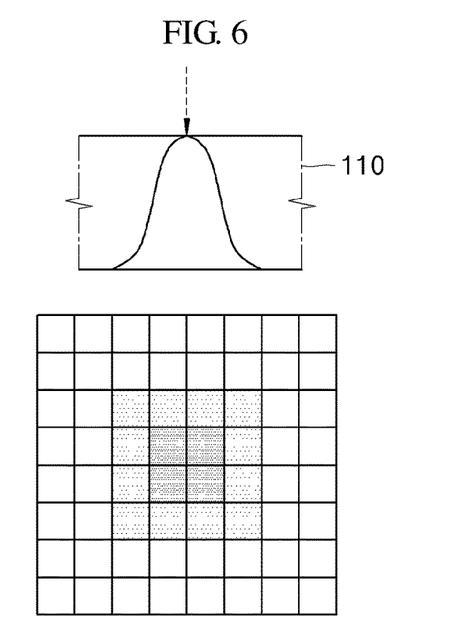
FIG. 6 is a conceptual diagram illustrating the magnitude of a PSF in a pixel array panel in which a pixel size is small according to an embodiment of the present invention.

FIG. 5 is a conceptual diagram illustrating the magnitude of a PSF in a pixel array panel in which a pixel size is large according to an embodiment of the present invention, and FIG. 6 is a conceptual diagram illustrating the magnitude of a PSF in a pixel array panel in which a pixel size is small according to an embodiment of the present invention.

Referring to FIGS. 5 and 6, the resolution of the radiographic image may vary according to the pixel size of the pixel array panel 120. FIGS. 5 and 6 have the same shadow area, but FIG. 5 does not represent well light and darkness for each position because of a large pixel size. However, in FIG. 6, since the pixel size is smaller than that of FIG. 5, the light and darkness of a peripheral portion may be represented low to show the light and darkness for each position relatively well. Like this, the smaller the pixel size is, the higher the resolution is.

The parameter may define the magnitude of the PSF and the shape of the PSF. Here, the magnitude and shape of the PSF are parameters for depicting a scattering type of light in a situation in which the scattering type of light is quantized by the scintillator panel 110 and converted to a digital signal.

The magnitude of the PSF may mean the number of pixels (or the size of a matrix) having a digital value, and may correspond to the number of pixels corresponding to an area on which a point of light is scattered by the scintillator panel 110. Accordingly, for the same scintillator panel 110, when the pixel size of the pixel array panel 120 is large, since the number of pixels corresponding to the area on which the point of light is scattered by the scintillator panel 110 is smaller than that in a case where the pixel size of the pixel array panel 120 is small, the size of the PSF may be relatively smaller. Since the magnitude of the PSF is required to be sufficiently large to include the area on which the light is scattered by the scintillator panel 110, the magnitude of the PSF may vary according to the pixel size of the pixel array panel 120.

The shape of the PSF may be that of a graph formed by each pixel value (or matrix value) of the PSF. The shape of the PSF may be determined by a matrix of the PSF. A variation amount of the brightness of an image may vary for each area according to the shape (or matrix) of the PSF. Through this, various blurring effects may be obtained by applying the PSF to a sharp image, and correction may be effectively performed according to a blurring type by varying the shape of the PSF and performing deconvolution according to a blurring shape of a radiographic image.

In an embodiment of the present invention, the PSF shape may be a Gaussian shape. For example, when the radiation 10 collides with the scintillator 111, since visual light is radiated from the scintillator 111 in all directions, it may be effective to determine the shape of the PSF as a Gaussian shape which may represent dispersion well from one point to all directions. However, the PSF shape is not limited thereto and may be determined according to the blurring type of the radiographic image.

In a case where the PSF shape is the Gaussian shape, the Gaussian shape may be determined by sigma σ of the Gaussian distribution and the sigma σ of the Gaussian distribution may be used as one of the parameters. Accordingly, in the PSF of the Gaussian shape, the magnitude of the PSF and the sigma σ of the Gaussian distribution may be used as the parameters.

The PSF of the Gaussian shape may be expressed as the following Equation $$G(x, y, \sigma) = \frac{1}{2\pi\sigma^2} e^{\frac{-(x^2+y^2)}{2\sigma^2}} \quad (1)$$

In Equation (1), x and y denote x and y coordinates, σ denotes sigma of the Gaussian distribution, and when x, y, and σ are substituted for Equation (1), a Gaussian value at (x, y) coordinates may be obtained.

Furthermore, the thicker the thickness of the scintillator panel 110 is, the magnitude of the PSF and the sigma σ of the Gaussian distribution may increase, and a blurring area may be increased since the visible light 11 emitted from the scintillator 111 in all directions may be dispersed wider before being incident to the photodiode 121. Accordingly, since the magnitude of the PSF may be increased and the sigma σ of the Gaussian distribution may be increased according to the magnitude of the PSF, the blurring may be effectively depicted through the PSF. In addition, the magnitude and shape of the PSF may be obtained by expanding an LSF two-dimensionally after obtaining the LSF in one dimension from an edge image.

Like this, the magnitude of the PSF may vary according to the pixel size of the pixel array panel 120, the thickness of the scintillator panel 110, and the type of the scintillator 111, and when the magnitude of the PSF is determined, the sigma σ of the Gaussian distribution may vary according to the thickness of the scintillator panel 110 and the type of the scintillator 111. Accordingly, in the present invention, the magnitude of the PSF and the sigma σ of the Gaussian distribution may be obtained according to the pixel size of the pixel array panel 120, the thickness of the scintillator panel 110, and the type of the scintillator 111, and accordingly, a radiographic image having the best sharpness may be obtained with effective correction.

Next, the radiographic image is corrected by deconvoluted using the PSF, to which the parameter values are applied (operation S300). Once the parameter values are known, the radiographic image may be deconvoluted with the PSF to correct the radiographic image. Under assumption that an image including the blurring is generated by convoluting the PSF with a sharp image, the deconvolution process may be performed by iterating an algorithm until a residual error value between a blurred image obtained from capturing (namely, including light scattering by the scintillator) and a blurred image estimated by a user becomes sufficiently small. As the deconvolution, a spatial-invariant deconvolution for recovering the entire image using one PSF may be used. Alternatively, a spatial-variant deconvolution for recovering an image using multiple individual PSFs according to an image position may also be used. Although the spatial-variant deconvolution, in which an individual PSF is used properly to each position, may have higher sharpness than the spatial-invariant deconvolution, since a process for obtaining the individual PSF proper to each position is complicated, the spatial-invariant deconvolution may be mainly used.

The indirect radiation detector has a higher Detective Quantum Efficiency (DQE) but lower sharpness (or an MTF) than the direct radiation detector. Here, the DQE is a radiation conversion efficiency, and means that a good image may be obtained using a smaller radiation dose when the DQE becomes higher. Accordingly, when the indirect radiation detector is used in the present invention, scintillator scattering occurring due to a structural feature of hardware may be corrected with a software algorithm to obtain high sharpness similar to that in the direct radiation detector while maintaining the high DQE of the indirect radiation detector.

As a result of performing the algorithm according to the present invention, an image may be obtained which has a higher DQE than that of the direct radiation detector, while having high sharpness. In this case, a sharper image of high quality may be obtained with a smaller radiation dose. In other words, in a case of being used in a product having a high DQE, since the radiation dose becomes smaller, a radiation exposure dose to a subject becomes lowered, and since a sharper image may be obtained when the sharpness is high, it is useful to diagnosis.

In particular, in mammography, even a very detailed part may be observed with a sharper radiographic image in a process for observing microcalcification and breast masses, etc.

Furthermore, in the present invention, it is assumed that the thickness of the scintillator panel 110 is uniform across the entire region of the radiation detector and a difference in thickness is not large, recovery may be performed by deconvolution using one PSF and the obtained image. In this process, image measurement evaluation factors such as the NNPS and DQE may vary according to a radiation dose irradiated at the time of obtaining the image. However, an increase in MTF according to the present invention does not influence the radiation dose. The MTF is influenced by the pixel size of the pixel array panel 120 and the structure (e.g. a needle structure of CsI) of the scintillator panel 110. Accordingly, in the present invention, the MTF, which is lowered by the structure of the scintillator panel 110, may be recovered to improve the sharpness of the radiographic image. Like this, an effect due to scattering of light generated in the scintillator panel 110 may determined through the MTF which is not influenced by the radiation dose, instead of variables influenced by the radiation dose such as the NNPS for determining a noise component and the DQE for determining the entire performance. In addition, the sharpness of the radiographic image may be improved by enhancing the MTF. In addition, the MTF is proper as a factor for measuring the sharpness of the radiographic image since it is not influenced by the radiation dose. Accordingly, in the present invention, the sharpness of the radiographic image is measured through the MTF and is improved by enhancing the MTF. When the factor for measuring the sharpness of the radiographic image is influenced by the radiation dose, it becomes difficult to measure the sharpness of the radiographic image. However, in the present invention, the sharpness of the radiographic image may be measured without any difficulty by using the MTF, which is not influenced by the radiation dose, as the measuring factor, and may be improved by enhancing the MTF.

Figure 7:
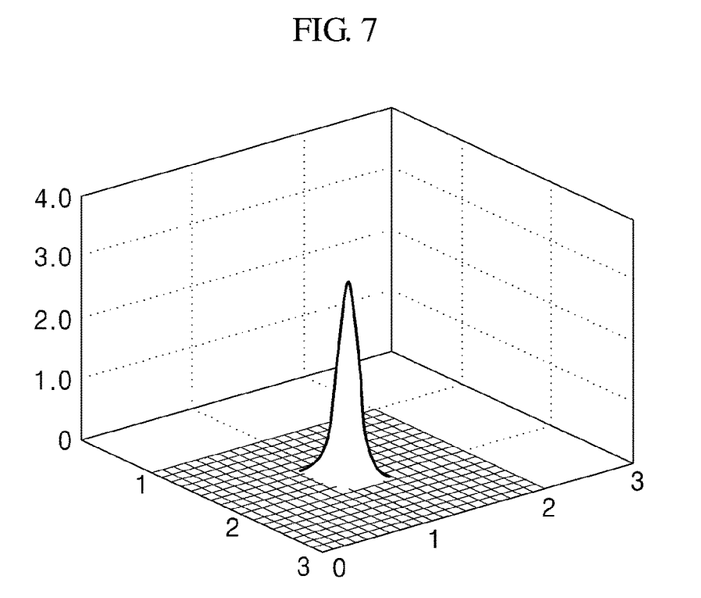
FIG. 7 illustrates a PSF of Gaussian type according to an embodiment of the present invention.

FIG. 7 illustrates a PSF of Gaussian type according to an embodiment of the present invention.

Referring to FIG. 7, scales in dotted lines denote an x-axis, a y-axis, and a pixel value (or a z-axis value) in an image, the total area of the pixels divided with solid lines becomes the magnitude of PSF, and combinations of pixel values become a matrix of the PSF. Here, the pixel value may be a brightness value of each pixel.

When the sharp image is convoluted with the PSF having such a Gaussian shape, a blurring may occur around the center portion of the Gaussian distribution. In addition, when the radiographic image including the blurring is deconvoluted with such a Gaussian type PSF, the blurring occurring around the center portion of the Gaussian distribution is mitigated to correct the radiographic image.

In operation S200 for determining the parameter value, a correction image for which the radiographic image is deconvoluted with the PSF may be determined as a parameter value for satisfying the image quality reference. When the radiographic image is corrected by deconvolution, the sharpness of the correction image may be enhanced than that of the radiographic image. However, when the sharpness is excessively artificially enhanced, unique features of the radiographic image become distorted. In addition, when the unique features of the radiographic image are distorted, since the radiographic image becomes worthless, the correction image of which unique features are distorted may be filtered out by evaluating the quality of the correction image and determining whether the unique features of the radiographic image are distorted. Accordingly, when the parameter value is determined as a parameter value for satisfying the image quality reference, the radiographic image may be corrected to the correction image of which the sharpness is enhanced without distorting the unique features of the radiographic image.

The image quality may be evaluated by measuring at least any one selected from among the MTF, the DQE, the NNPS, and a signal to noise ratio (SNR). The values of the MTF, DQE, NNPS, and SNR may be measured with an image evaluation tool by analyzing a feature graph of each measurement value to evaluate the image quality. In other words, whether the unique features of the radiographic image are distorted may be determined through the feature graph of each measurement value.

The Modulation Transfer Function (MTF) represents a frequency response of any one image system and is a sharpness related measurement factor which may be defined as an image contrast ratio for a subject contrast. In addition, the MTF is a frequency recording capability for a region corresponding to each frequency when a spatial frequency of an image is measured, and the resolution of the image may be obtained by marking a degree that a radiography system reacts to a spatial variation of the image. The MTF is frequently used for evaluating the sharpness of an image and whether the sharpness is enhanced may be determined through the MTF.

The DQE represents a transfer feature of the SNR and is a parameter for representing a noise amount occurring by a last image. In other words, it measures the overall SNR performance of a radiation detector, and a capability of a radiation detector for transferring the SNR. In addition, the DQE may be defined as the square of a ratio of an output SNR to an input SNR, and may be expressed as Equation (2).

$$DQE(f) = \frac{MTF^2}{(SNR_{input} \cdot X)NNPS} \quad (2)$$

wherein X denotes a irradiation dose.

In addition, the DQE is a comprehensive index for indicating quality of a radiographic image and is obtained by the MTF, NNPS, and SNR. Accordingly, the image quality may be comprehensively evaluated with the MTF, NNPS, and SNR, and whether the unique features of the image are distorted may be effectively determined.

The noise power spectrum (NPS) is representation of a distribution of dispersion value of noise on a spatial frequency, represents dependence of noise on the spatial frequency, which is a variation factor between pixels in an image, and is a noise related measurement factor. And, the Normalized Noise Power Spectrum (NNPS) is a normalized NPS and may be obtained by averaging all spectrum samples.

Image noise means uncertainty or inaccuracy in an image signal, and may be divided into noise resulted from the number of photons forming image information and noise caused by an image signal processing circuit. For the former, a degree of the uncertainty increases when the number of photons forming the image information is small. On the other hand, when the number of photons increases, a probability to be detected as an image signal may become high to reduce a noise effect to the image signal. In order to evaluate the SNR of the radiography system, an image may be obtained using a lead phantom from which the central portion is removed, and may use gray-scale value of the obtained image, which is measured along a leader line. The image signal means a difference ΔD between a peripheral lead phantom and a gray-scale value in a circular region of the center, and the image noise means a standard deviation s of the gray-scale value of the obtained image. A ratio of them (ΔD/s) may be defined as the SNR which is a measurement factor related to the signal and noise.

Figure 8:
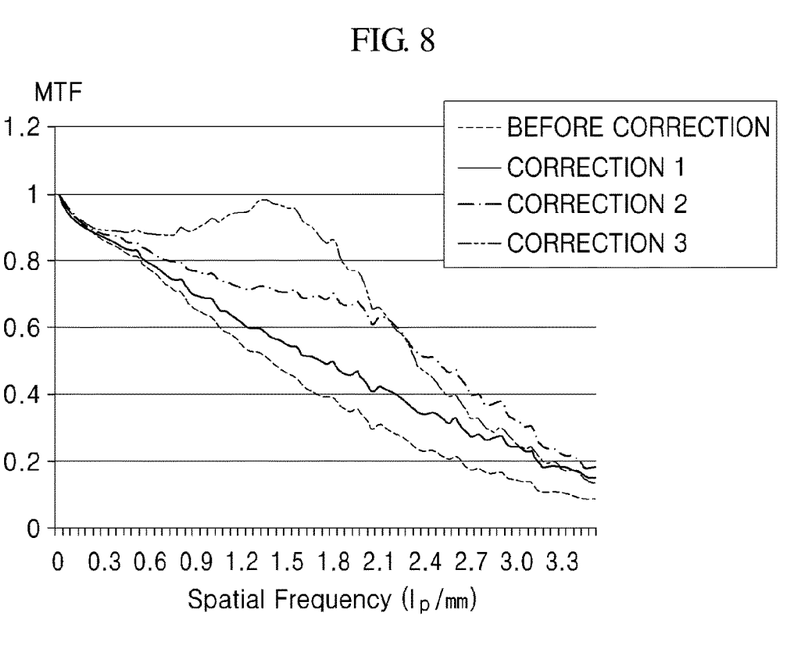
FIG. 8 is a graph for explaining a reference for selecting a parameter value of a PSF according to an embodiment of the present invention.

FIG. 8 is a graph for explaining a reference for selecting a parameter value of a PSF according to an embodiment of the present invention.

The indirect radiation detector has a higher DQE but lower sharpness (or a MTF) than the direct radiation detector. Accordingly, it is required to obtain high sharpness while maintaining the high DQE of the indirect radiation detector. Accordingly, when determining the parameters, in order to effectively determine the magnitude of the PSF and the sigma σ of the Gaussian distribution, the MTF which is an index for checking the sharpness with reference to the image quality may be firstly checked.

Referring to FIG. 8, the image quality reference may include a condition that a value of the MTF for a spatial frequency of the correction image decreases according to an increase in spatial frequency, and the MTF value is the highest in the correction image according to the parameter value. It may be confirmed that in a graph of the radiographic image (before correction), the MTF value decreases in a right downward direction as the spatial frequency increases. Like this, in the radiographic image (before correction) including the blurring, when the spatial frequency increases, the blurring is amplified to decrease the MTF. However, unlike the obtained radiograph image (before correction), a graph of correction 3 does not have a right downward slope in a certain period (where the spatial frequency is about 0.7 lp/mm to about 1.4 lp/mm), but tilts upward. From the graph of correction 3, it may be estimated that the unique features of the radiograph image are distorted. In order to verify this, the DQE may be analyzed. From the graph of correction 3 of which the shape is greatly changed, it may be seen that a difference occurs between DQE values of the correction image and the radiographic image, and the unique features thereof are distorted. Although a graph of correction 2 is slightly changed in shape from the radiographic image (before correction), it has a right downward slop. From the analysis of the graph of correction 2, it may be seen that the correction image maintains the DQE value of the radiographic image and the unique features of the radiographic image are not distorted. Like this, whether the unique features of the radiographic image are distorted may be determined through the graph of the MTF. In other words, whether the unique features of the radiographic image are distorted may be determined by determining whether the MTF graph does not have the right downward slope but tilts upward. Furthermore, whether the unique features of the radiographic image are distorted may also be determined not only with the MTF graph but also with the NNPS and SNR graphs.

In addition, a correction image having a highest MTF value among the correction images corrected according to the parameter value may be set as the image quality reference. For example, when the MTF value of the correction image is the highest, since the sharpness thereof is best, a correction image of which the sharpness is the best may be obtained among the correction images. However, since it is not good that the sharpness becomes so high to distort the unique features of the radiographic image, a correction image having the highest MTF value may be selected from among the correction images of which the DQE value of the radiographic image is maintained. In addition, a parameter may be determined so that the obtained radiographic image may be deconvoluted with the correction image satisfying the foregoing condition. Accordingly, the correction image of which the unique features of the radiographic image are not distorted and which has the highest sharpness may be obtained. Like this, in the present invention, since a sharp radiographic image may be obtained only with a small radiation dose and a radiation exposure dose of a subject may be reduced accordingly, more accurate diagnosis may be performed with the sharp radiographic image. In particular, in mammography, even a very detailed part may be observed with a sharper radiographic image in a process for observing microcalcification and breast masses, etc.

FIG. 8 is a graph obtained by changing the sigma σ of the Gaussian distribution while fixing the magnitude of the Gaussian type PSF, and a graph of correction 1 is for the case where σ=0.5, a graph of correction 2 is for the case where σ=0.7, and a graph of correction 3 is for the case where σ=1.0. From among the graphs of correction 1, correction 2, and correction 3, the graph of correction 2 may be selected. The reason is because although the graph of correction 3 has a highest MTF value, the unique features of the radiographic image are distorted. Therefore, the graph of correction 2 having a higher MTF value is selected from between the graphs of which the unique features of the radiographic image are not distorted. Accordingly, the sigma σ of the Gaussian distribution may be determined as 0.7, and the fixed magnitude of the PSF may be determined as the parameter value. Furthermore, other parameter values may be determined through experiments according to the above-described methods.

Figure 9:
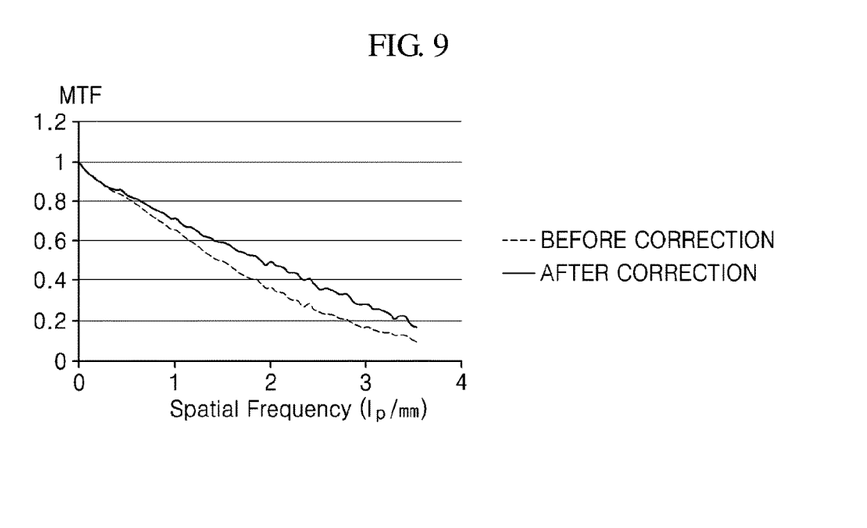
FIG. 9 is a graph of a modulation transfer function (MTF) for evaluating image quality according to an embodiment of the present invention.
Figure 10:
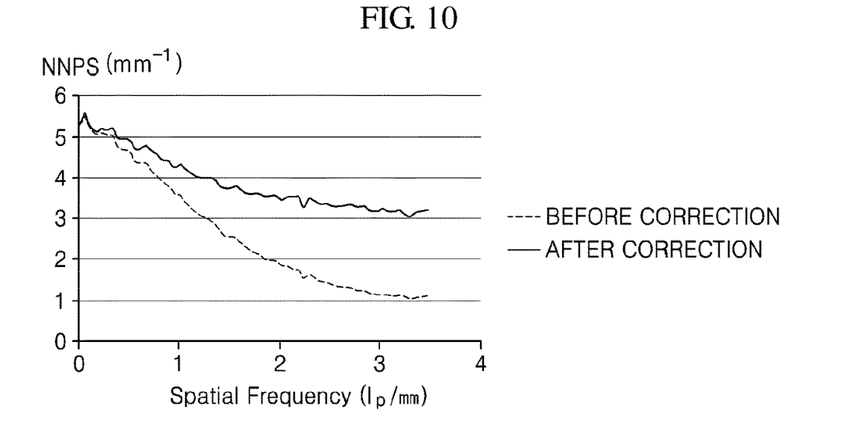
FIG. 10 is a graph of a normalized noise power spectrum (NNPS) for evaluating image quality according to an embodiment of the present invention.
Figure 11:
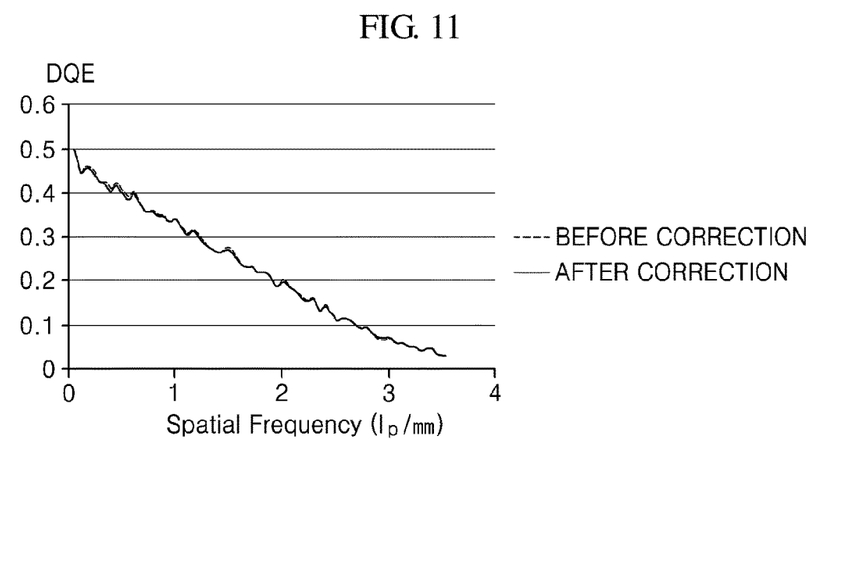
FIG. 11 is a graph of a detective quantum efficiency (DQE) for evaluating image quality according to an embodiment of the present invention.

FIG. 9 is a graph of an MTF for evaluating image quality according to an embodiment of the present invention, FIG. 10 is a graph of an NNPS for evaluating image quality according to an embodiment of the present invention, and FIG. 11 is a graph of a DQE for evaluating image quality according to an embodiment of the present invention.

Referring to FIGS. 9 to 11, in the correction image for satisfying the image quality reference, not only a graph of the MTF, which is a measurement factor of sharpness, but also a graph of the NNPS increases. Therefore, the DQE graph is not nearly changed. As a result, the correction image for satisfying the image quality reference has the same DQE as the radiographic image before correction. This means that the unique features of the correction image are the same as those of the radiographic image, and the unique features of the radiographic image are not distorted by the correction. Accordingly, the radiographic image, of which the sharpness is improved, may be obtained while characteristics of the indirect radiation detector, in which the DQE is high, are maintained, and accordingly, a sharp radiographic image may be obtained with a small radiation dose. Through this, a radiation exposure dose of a subject may be reduced and more accurate diagnosis may be performed with the sharp radiographic image. In particular, in mammography, even a very detailed part may be observed with a sharper radiographic image in a process for observing microcalcification and breast masses, etc.

The image quality reference may include a condition that the DQE value of the correction image is in the range of 90% to 110% of the DQE value of the radiographic image in the same spatial frequency. The DQE is obtained from the MTF, NNPS, and SNR. Accordingly, the DQE is for comprehensively evaluating the image quality by including the MTF, NNPS, and SNR, and may effectively determine whether the unique features of the image are distorted. Since a change in DQE due to correction of the radiographic image means distortion of the unique features of the radiographic image, the DQE value should not be changed. However, since it is difficult to equally maintain the DQE without an error while changing the MTF, an error range of ±10% may be tolerated. When the DQE value of the correction image is in the range of 90% to 110% of the DQE value of the radiographic image in the same spatial frequency, the DQE graph of the correction image may be maintained in the same type as the obtained DQE graph of the radiograph image. Since there is a little difference in DQE value in this case, unique features of the correction image and the obtained radiographic image may be determined as the same. On the other hand, when the DQE value of the correction image is out of the range of 90% to 110% of the DQE value of the radiographic image in the same spatial frequency, the DQE graph of the correction image may vary differently from the obtained DQE graph of the radiograph image. In addition, since the difference in DQE value is large, the unique features of the correction image may be determined to be distorted. Like this, since the correction image, which does not satisfy the condition that the DQE value of the correction image is in the range of 90% to 110% of the DQE value of the radiographic image in the same spatial frequency, is an image of which the unique features are distorted, it is worthless as an image for medical diagnosis. Therefore, the correction image necessarily satisfies the condition that the DQE value of the correction image is in the range of 90% to 110% of the DQE value of the radiographic image in the same spatial frequency.

Although the DQE value condition is a prerequisite that the correction image should satisfy, since the DQE may be obtained from the MTF, NNPS, and SNT, the DQE value is not a value preferentially checked. For example, the MTF, from which the sharpness may be determined, may be firstly checked, and then distortion of the unique features of the radiographic image may be estimated from the MTF graph. However, it is necessary to check the DQE in order to accurately determine whether the unique features of the radiographic image are distorted.

Furthermore, images for measuring the NNPS and MTF may be different from each other. The image for measuring the NNPS may be captured without a subject, and the image for measuring the MTF may be obtained by capturing an edge subject. The NNPS is for measuring and analyzing noise displayed as white in the image captured without an object. In addition, the MTF is for determining whether a subject portion is distinguished from a portion without the subject at the edge portion of the subject and for determining an extent of blurring. Through this, the NNPS and the MTF are measured, and the DQE may be calculated from the NNPS and MTF.

An operation for classifying and storing the determined parameter values according to at least any one among the pixel size of the pixel array panel 120, the thickness of the scintillator panel 110, and the type of scintillator 111 is further included. In operation S300 for correcting the radiographic image by deconvoluting the radiographic image, from among the stored parameter values, the parameter value is selected according to at least any one among the pixel size of the pixel array panel 120, the thickness of the scintillator panel 110, and the type of scintillator 111, which are used for obtaining the radiographic image, and the radiographic image may be corrected. A lot of time are necessary to verify whether a correction image, for which the radiographic image is deconvolutioned with a PSF to which the parameter values are applied, satisfies the image quality reference. Accordingly, parameter data may be generated in advance according to at least one among the pixel size of the pixel array panel 120, the thickness of the scintillator panel 110, and the type of the scintillator 111. In addition, the parameter value, which corresponds to at least any one among the pixel size of the pixel array panel 120, the thickness of the scintillator panel 110, and the type of the scintillator 111, is selected and applied to the PSF.

The parameter data may be obtained by, before operation S100 for obtaining the radiographic image, applying all the parameter values to each one among the pixel size of the pixel array panel 120, the thickness of the scintillator panel 110, and the type of the scintillator 111 to generate correction images, determining whether the correction images satisfy the image quality reference, and by storing the parameter values for allowing the correction images to satisfy the image quality reference according to at least any one among the pixel size of the pixel array panel 120, the thickness of the scintillator panel 110, and the type of the scintillator 111. Accordingly, through the parameter data, combinations of corresponding parameter values may be obtained according to at least one among the pixel size of the pixel array panel 120, the thickness of the scintillator panel 110, and the type of the scintillator 111. In addition, a correction image of which unique features of the radiographic image are not distorted while having the high MTF graph may be easily obtained.

Furthermore, a parameter value satisfying the DQE condition and having a highest MTF value is searched while changing any one parameter and fixing other parameters, and for other parameters, parameter values satisfying the DQE condition and having a highest MTF value are searched in the same manner, and then a combination of parameter values, each having a highest MTF value and satisfying the DQE condition, may be obtained while the found parameter values are relatively changed. At this point, since the magnitude of the PSF is necessary to be determined only to be equal to or greater than a prescribed magnitude (e.g., the magnitude that sufficiently includes the physical range of scattering), the magnitude of PSF may be firstly determined through evaluation of the image quality after fixing other parameters. Next, the sigma σ of the Gaussian distribution may be determined by using the determined magnitude of PSF, and other parameters may be determined such that the DQE condition is satisfied and the MTF value is a highest while the determined magnitude of PSF and the sigma σ of the Gaussian distribution are fixed. The parameter value combination obtained like this may be the determined parameter values. In addition, the determined parameter values may be classified and stored according to at least one among the pixel size of the pixel array panel 120, the thickness of the scintillator panel 110, and the type of the scintillator 111, and the classified and stored parameter values may be the parameter data.

In operation S300 for correcting the radiographic image by deconvoluting the radiographic image, the deconvolution may be iterated using the PSF to which the parameter values are applied, and the radiographic image may be corrected. The parameter value combination is required not to distort the unique features of the radiographic image for the correction image at the time of deconvoluting the obtained radiographic image. Through this combination, even when the MTF graph is not high, the radiographic image may be corrected to a correction image having a highest MTF graph among the correction images in which the unique features of the radiographic image are not distorted by iterating deconvolution using the PSF to which the parameter values are applied. At this point, in order for the unique features of the radiographic image not to be distorted, the correction image is necessary to satisfy the condition that the DQE value of the correction image is in the range of 90% to 110% of the DQE value of the radiographic image in the same spatial frequency. Like this, the extent of correction of the radiographic image may be adjusted according to the magnitude of PSF, the shape of PSF, and the iteration number of deconvolution. In other words, the correction extent of the radiographic image may be determined according to the shape and magnitude of PSF and the number of times of devolution. Furthermore, through advance experiments, the number of iteration times of deconvolution may also be preset by checking a maximum number of times that the unique features of the radiographic image are not distorted with the parameter value combinations. In addition, the parameter value combination and the maximum number of iterations may be pre-stored in a lookup table, etc. according to at least any one among the pixel size of the pixel array panel 120, the thickness of the scintillator panel 110, and the type of the scintillator 111.

An operation for removing a fault element from the radiographic image may be further included before the operation for correcting the radiographic image by deconvoluting the radiographic image. The fault element may include a flat field, a gain, and a defect. Among them, the defect may mainly influence the radiographic image at the time of deconvoluting the radiographic image. The defect is a part to which a pixel value is not properly output. When there is a defect in the radiographic image at the time of deconvoluting the radiographic image, the defect is amplified to exert bad influence on quality of the radiographic image. Accordingly, the defect in the radiographic image may be removed before the radiographic image is corrected by deconvoluting the radiographic image.

At the time of removing the defect, the defect in a point/pixel type or a line type may be corrected using peripheral information. In this case, since correction is performed using the peripheral information, a pixel value similar to an actual pixel value may be obtained and accordingly the quality of the radiographic image may be improved. In addition, the defect is removed and accordingly, amplification of the defect may be prevented.

In addition, a flat field correction and a gain correction may be performed as a preprocessing procedure of the radiographic image. The flat field correction is to correct a difference in dose response of a pixel occurring by a hardware cause. In addition, the gain correction is to correct dose nonuniformity occurring by a radiation source.

Figure 12:
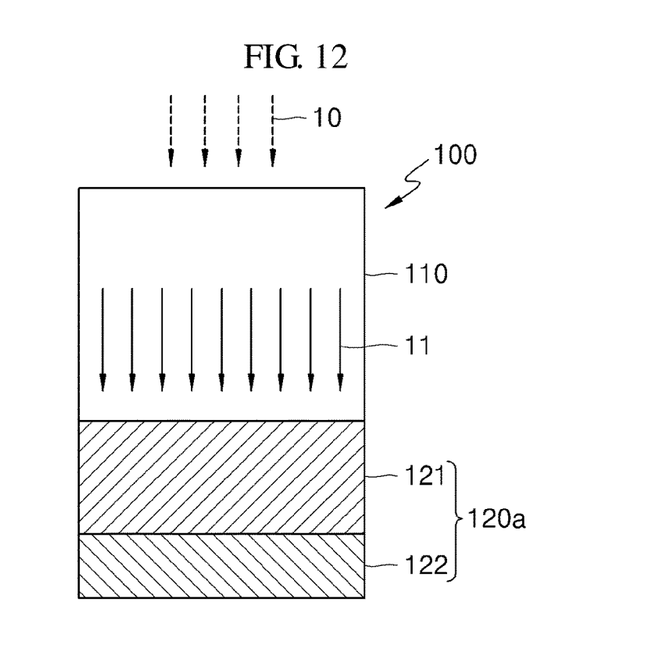
FIG. 12 is a cross-sectional view of a photodiode type indirect radiation detector according to another embodiment of the present invention.
Figure 13:
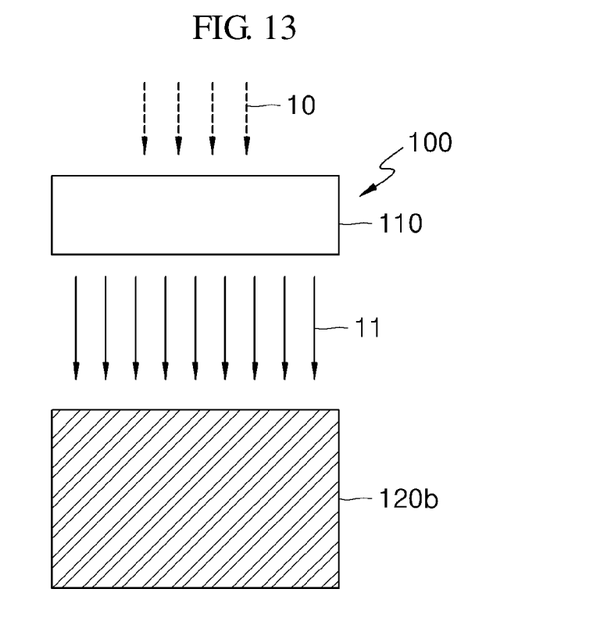
FIG. 13 is a cross-sectional view of a charge-coupled device type indirect radiation detector according to another embodiment of the present invention.

FIG. 12 is a cross-sectional view of a photodiode type indirect radiation detector according to another embodiment of the present invention, and FIG. 13 is a cross-sectional view of a charge-coupled device type indirect radiation detector according to another embodiment of the present invention.

Descriptions will be provided about a radiography system according to another embodiment with reference to FIGS. 12 and 13, and repetitive descriptions with the foregoing descriptions related to the method for processing a radiographic image according to the embodiment will be omitted.

A radiography system according to another embodiment may include a radiation irradiating unit for irradiating a radiation 10 on a subject; an indirect radiation detector 100 which includes a scintillator panel 110 for converting the radiation 10 passing through the subject to be incident to visible light 11 and a pixel array panel 120 for storing charges generated by the visible light 11 in each pixel, and which realizes a radiographic image according to a charge amount in each pixel; and an image processing unit for correcting the radiographic image by deconvoluting the radiographic image obtained by the indirect radiation detector 100 with an PSF.

The radiation irradiating unit may adjust the intensity of the radiation 10 and irradiate the radiation 10 of the certain intensity on the subject to allow the radiation 10 passing through the subject to be incident into the scintillator panel 110.

The indirect radiation detector 100 may include the scintillator panel 110. The radiation 10 incident to the scintillator panel 110 collides with the scintillator 111 to be converted to the visible light 11. Here, the indirect radiation detector 100 may convert the intensity of the visible light 11 to an electrical signal through a thin film transistor 122 in which a photodiode 121 or a charge coupled device 120b is installed, and may realize an image with the electrical signal.

The image processing unit may deconvolute a blurring of the radiographic image, which occurs by light scattered by the scintillator 111 of the scintillator panel 110, with a PSF, and correct the blurring. Through this, the sharpness of the radiographic image may be improved to enhance accuracy of medical diagnosis using the radiographic image.

The image processing unit may include a data storage unit in which parameter values, which are applied to a PSF according to at least any one among the pixel size of the pixel array panel 120, the thickness of the scintillator panel 110, and the type of the scintillator 111, are classified and stored according to at least any one among the pixel size of the pixel array panel 120, the thickness of the scintillator panel 110, and the type of the scintillator 111; a parameter selecting unit for selecting the parameter value according to at least any one among the pixel size of the pixel array panel 120, the thickness of the scintillator panel 110, and the type of the scintillator 111, and an image correcting unit for deconvoluting the radiographic image using the PSF to which the selected parameter value is applied.

The data storage unit may store combinations of the parameter values which are classified according to at least one among the pixel size of the pixel array panel 120, the thickness of the scintillator panel 110, and the type of the scintillator 111, and which satisfy a certain condition. When the parameter value combinations are applied to the PSF to deconvolute the radiographic image, a correction image in which unique features of the radiographic image are not distorted and which has a high MTF graph may be obtained. In addition, the parameter values, which correspond to at least any one among the pixel size of the pixel array panel 120, the thickness of the scintillator panel 110, and the type of the scintillator 111, may be easily selected.

The parameter selecting unit may select a parameter value according to at least any one among the pixel size of the pixel array panel 120, the thickness of the scintillator panel 110, and the type of the scintillator 111. Here, the parameter value may be selected according to at least any one among the pixel size of the pixel array panel 120, the thickness of the scintillator panel 110, and the type of the scintillator 111 by using the parameter values (i.e. parameter data), which stored in the data storage unit.

The image correcting unit may correct the radiographic image by deconvoluting the radiographic image using the PSF to which the selected parameter value is applied. The correction may be performed to mitigate the blurring by convoluting a radiographic image including a blurring with a sharp image to search a PSF which generates the same blurring as that in the radiographic image, and by deconvoluting the radiographic image including the blurring using the found PSF.

The image processing unit may further include an iteration setting unit for setting the number of iterations for deconvoluting the radiographic image. When the sharpness is slightly improved with one time deconvolution, the deconvolution may be iterated to improve the sharpness of the radiographic image. Like this, the iteration setting unit may allow the extent of correction of the radiographic image to be adjusted according to the number of times of deconvolution. Furthermore, through advance experiments, the number of times of deconvolution may also be preset by checking a maximum number of times that the unique features of the radiographic image are not distorted with the parameter value combinations. In addition, the parameter value combination and the maximum number of iterations may be pre-stored in the data storage unit, such as a lookup table, according to at least any one among the pixel size of the pixel array panel 120, the thickness of the scintillator panel 110, and the type of the scintillator 111.

The iteration setting unit may set the iteration number in order to satisfy the condition that the DQE value of the correction image, which is corrected by deconvoluting the radiographic image with the PSF, is in the range of 90% to 110% of the DQE value of the radiographic image in the same spatial frequency. When the DQE value of the correction image is out of the range of 90% to 110% of the DQE value of the radiographic image in the same spatial frequency, the unique features of the radiographic image in the correction image are distorted. Accordingly, the DQE value of the correction image may be allowed to be in the range of 90% to 110% of the DQE value of the radiographic image in the same spatial frequency. However, too many iteration of the deconvolution for improving the sharpness may cause distortion in unique features of the radiographic image. Accordingly, the iteration number may be set in order to satisfy the condition that the DQE value of the correction image is in the range of 90% to 110% of the DQE value of the radiographic image in the same spatial frequency.

The image processing unit may further include a preprocessing unit for removing a fault element from the obtained radiographic image. The preprocessing unit may preprocess the obtained radiographic image. When there is a fault element such as a defect in the radiographic image at the time of deconvolution of the radiographic image, the fault element such as the defect may be amplified to exert a bad effect to the quality of the radiographic image. Accordingly, the fault element such as defect in the radiographic image may be removed before the radiographic image is corrected by deconvoluting the radiographic image. The fault element may include not only the defect but also a flat field and a gain, and the defect may mainly influence on the radiographic image at the time of deconvoluting the radiographic image.

Like this, a blurring of a radiographic image due to scatting of light generated in a scintillator panel of an indirect type radiation detector may be corrected by deconvoluting the radiographic image with the PSF. Accordingly a radiographic image of which the sharpness is improved with the indirect radiation detector may be obtained. In addition, since a radiographic image for which the sharpness is improved with the indirect radiation detector having a high DQE is obtained, a sharp radiographic image may be obtained even with a small radiation dose. Accordingly, a radiation exposure dose of a subject may be lowered and more accurate diagnosis may be performed with the sharp radiographic image. In particular, in mammography, even a very detailed part may be observed with a sharper radiographic image in a process for observing microcalcification and breast masses, etc.

In addition, artificial improvement in sharpness may be prevented and only a blurring may be corrected by evaluating quality of a radiographic image for which the blurring is corrected. In addition, a parameter value having highest sharpness may be easily obtained while the image quality is satisfied according to the thickness of the scintillator panel using parameter data. Furthermore, amplification of a defect factor may be prevented in a process for correcting a blurring of a radiographic image through preprocessing the radiographic image for removing the fault element before correcting the blurring of the radiographic image. In addition, since the blurring is not artificially deleted but is mitigated to disappear, loss of data information on the radiographic image may be prevented.

Although the method for processing radiographic image and the radiography system have been described with reference to the specific embodiments, they are not limited thereto. Therefore, it will be readily understood by those skilled in the art that various modifications and changes can be made thereto without departing from the spirit and scope of the present invention defined by the appended claims and their equivalents.

What is claimed is:

1. A method for processing a radiographic image comprising:
   obtaining a radiographic image using an indirect radiographic detector comprising a scintillator panel and a pixel array panel;
   determining a parameter value for defining a point spread function (PSF) according to the scintillator panel or the pixel array panel; and
   correcting the radiographic image by deconvoluting the radiographic image using the PSF to which the parameter value is applied;
   wherein, in the determining the parameter value, the parameter value is determined to allow a correction image for which the radiographic image is deconvoluted using the PSF to satisfy an image quality reference, and
   the image quality reference comprises a condition that for a spatial frequency of the correction image, a value of a modulation transfer function (MTF) decreases according to an increase in spatial frequency, and the value of the MTF is a highest in the correction image according to the parameter value.

2. The method of claim 1, further comprising removing a fault element from the radiographic image before the correcting the radiographic image by deconvoluting the radiographic image.

3. The method of claim 1, wherein the parameter defines a magnitude of the PSF and a shape of the PSF.

4. The method of claim 1, wherein the image quality is evaluated by measuring at least any one selected from among the MTF, a detective quantum efficiency (DQE), a normalized noise power spectrum (NNPS), and a signal to noise ratio (SNR).

5. The method of claim 1, wherein the image quality reference comprises a condition that a DQE value of the correction image is in a range of 90% to 110% of a DQE value of the radiographic image in a same spatial frequency.

6. The method of claim 1, further comprising:
classifying and storing the determined parameter value according to at least any one among a pixel size of the pixel array panel, a thickness of the scintillator panel, and a type of the scintillator,
wherein in the correcting the radiographic image by deconvoluting the radiographic image, the radiographic image is corrected by selecting a parameter value from among stored parameter values according to at least any one among the pixel size of the pixel array panel, the thickness of the scintillator panel, and the type of the scintillator, which are used for obtaining the radiographic image.

7. The method of claim 1, wherein in the correcting the radiographic image by deconvoluting the radiographic image, the radiographic image is corrected by iterating the deconvolution using the PSF to which the parameter value is applied.

8. A radiography system comprising:
a radiation irradiating unit irradiating a radiation on a subject;
an indirect radiation detector comprising a scintillator panel converting a radiation, which passes through the subject and is incident thereto, to a visible light, and a pixel array panel storing charges generated by the visible light in each pixel, and realizing a radiographic image according to a charge amount in each pixel; and
an image processing unit correcting the radiographic image by deconvoluting the radiographic image obtained by the indirect radiation detector using a point spread function (PSF);
wherein the image processing unit comprises an iteration setting unit setting a number of times of deconvoluting the radiographic image, and
the iteration setting unit sets an iteration number for satisfying a condition that a DQE value of a correction image, which is corrected by deconvoluting the radiographic image with the PSF, is in a range of 90% to 110% of a DQE value of the radiographic image in a same spatial frequency.

9. The radiography system of claim 8, wherein the image processing unit further comprises:
a data storage unit in which a parameter value, which is applied to the PSF according to at least any one among a pixel size of the pixel array panel, a thickness of the scintillator panel, and a type of the scintillator, is classified and stored according to at least any one among the pixel size of the pixel array panel, the thickness of the scintillator panel, and the type of the scintillator;
a parameter selecting unit selecting the parameter value according to the at least any one among the pixel size of the pixel array panel, the thickness of the scintillator panel, and the type of the scintillator; and
an image correcting unit deconvoluting the radiographic image using the PSF to which the selected parameter value is applied.

10. The radiography system of claim 8, wherein the image processing unit further comprises a preprocessing unit removing a fault element from the obtained radiographic image.

* * * * *